United States Patent
Kochy et al.

(10) Patent No.: US 7,320,775 B2
(45) Date of Patent: Jan. 22, 2008

(54) EXCHANGEABLE FLOW CELL ASSEMBLY WITH A SUSPENDED CAPILLARY

(75) Inventors: Thomas E. Kochy, Redwood City, CA (US); Roger A. O'Neill, San Carlos, CA (US); Terah W. Smiley, Walnut Creek, CA (US); Vidal O. Smith, Newark, CA (US)

(73) Assignee: Guava Technologies, Inc., Hayward, CA (US)

( * ) Notice: Subject to any disclaimer, the term of this patent is extended or adjusted under 35 U.S.C. 154(b) by 775 days.

(21) Appl. No.: 10/146,019

(22) Filed: May 14, 2002

(65) Prior Publication Data

US 2003/0017076 A1    Jan. 23, 2003

Related U.S. Application Data

(60) Provisional application No. 60/291,541, filed on May 16, 2001.

(51) Int. Cl.
- G01N 15/06    (2006.01)
- G01N 33/00    (2006.01)
- G01N 33/48    (2006.01)
- G01N 1/10     (2006.01)
- G01N 21/01    (2006.01)

(52) U.S. Cl. .................. 422/68.1; 422/50; 422/55; 422/81; 422/82; 422/82.05; 422/99; 422/100; 422/101; 422/102; 422/103; 422/104; 436/43; 436/52; 436/164; 436/172; 73/1.01; 73/1.02; 73/53.01; 435/287.1; 435/287.3; 435/288.7; 356/244; 356/246; 204/601

(58) Field of Classification Search .................. 422/50, 422/55, 68.1, 81, 82, 82.05, 99, 100, 101, 422/102, 103, 104; 436/43, 52, 164, 172; 73/1.01, 1.02, 53.01; 435/287.1, 287.3, 288.7; 204/601; 211/13.1; 356/244, 246
See application file for complete search history.

(56) References Cited

U.S. PATENT DOCUMENTS

| | | | | |
|---|---|---|---|---|
| 3,917,404 A | * | 11/1975 | Heiss | 356/317 |
| 5,439,288 A | | 8/1995 | Hoffman et al. | |
| 6,473,171 B1 | * | 10/2002 | Buttry et al. | 356/246 |
| 6,572,752 B1 | * | 6/2003 | Maeshima et al. | 204/601 |
| 6,816,257 B2 | * | 11/2004 | Goix | 356/318 |
| 2002/0028434 A1 | | 3/2002 | Goix et al. | |

FOREIGN PATENT DOCUMENTS

| | | |
|---|---|---|
| EP | 0 412 431 A2 | 2/1990 |
| WO | WO 01/42763 A1 | 10/2000 |
| WO | PCT/US 02/15731 | 5/2002 |

OTHER PUBLICATIONS

European Patent Office (EPO) Communication under Rule 51(4) EPC, for European Application No. 02739288, dated Apr. 26, 2007.

* cited by examiner

*Primary Examiner*—Brian Sines
(74) *Attorney, Agent, or Firm*—Foley & Lardner LLP

(57) ABSTRACT

There is provided a flow cell assembly in which a shuttle supports and positions a capillary with its end extending beyond the shuttle. The flow cell assembly facilitates the replacement of a flow cell which is damaged or with flow cells having capillaries of different size or shape.

12 Claims, 4 Drawing Sheets

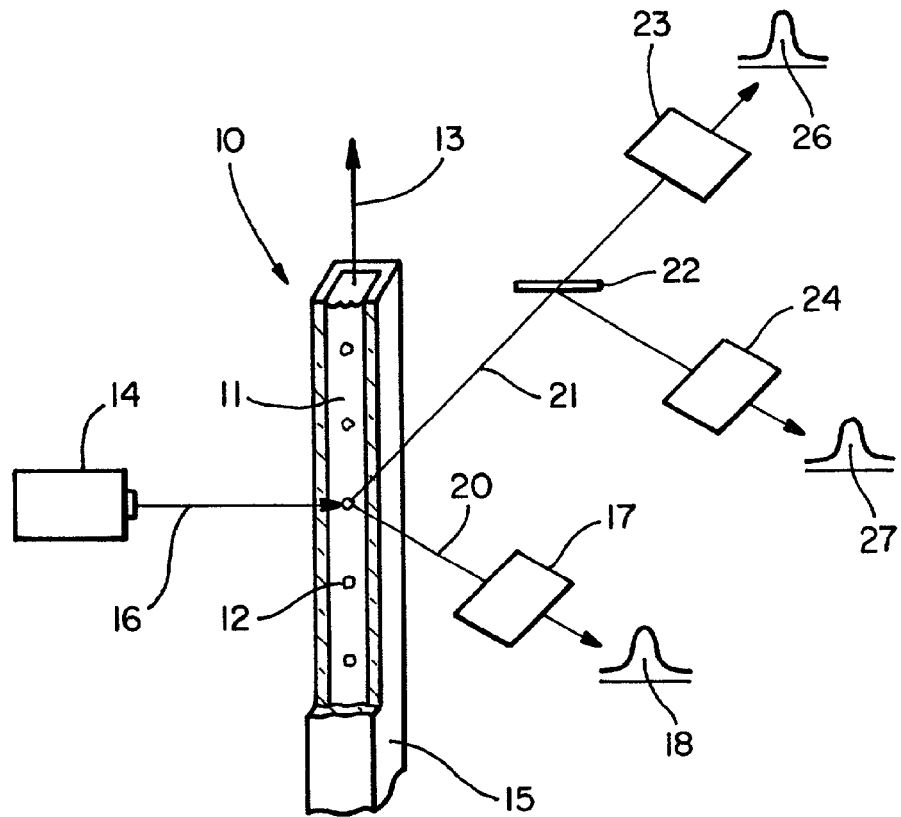
FIG_1
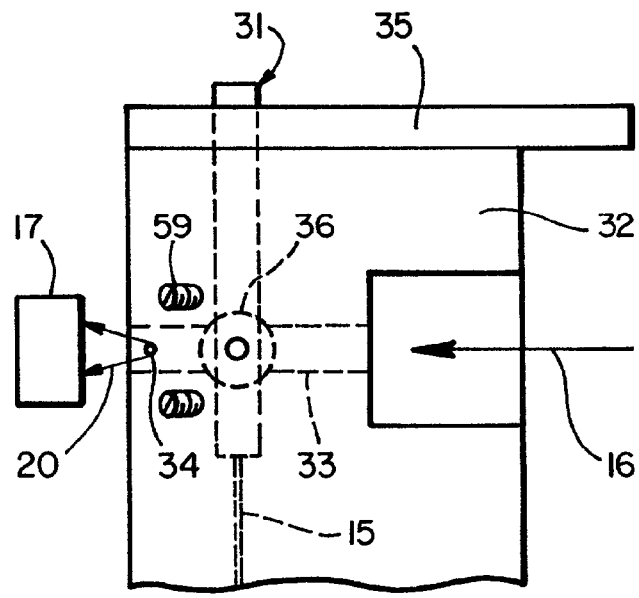
FIG_2

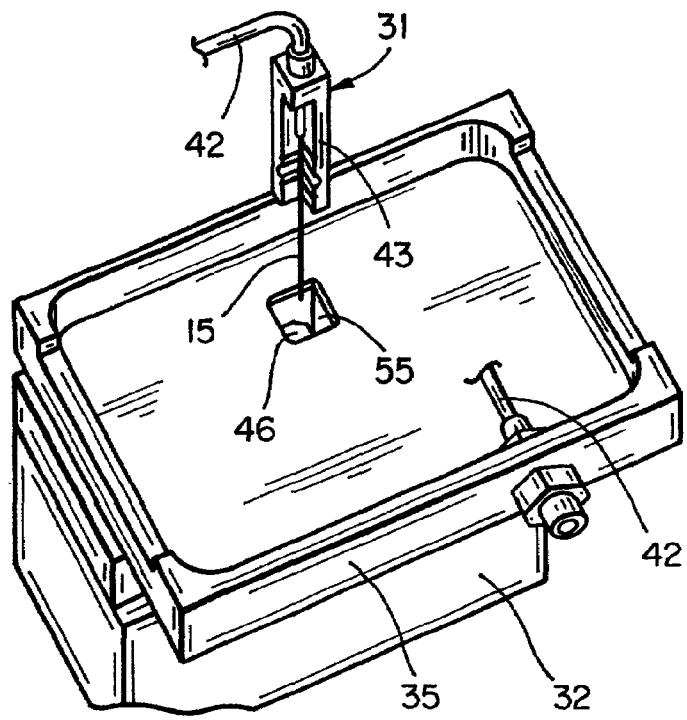
FIG_3
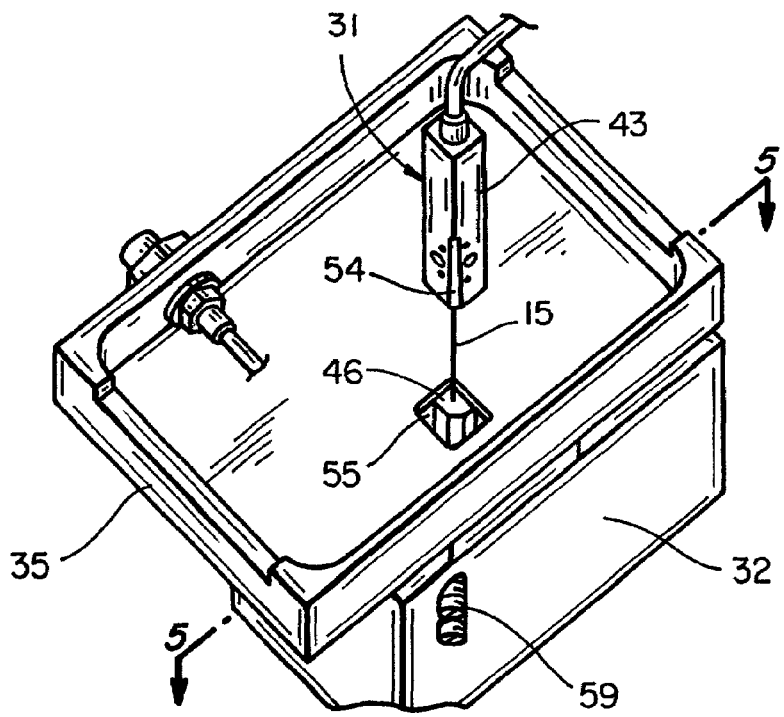
FIG_4

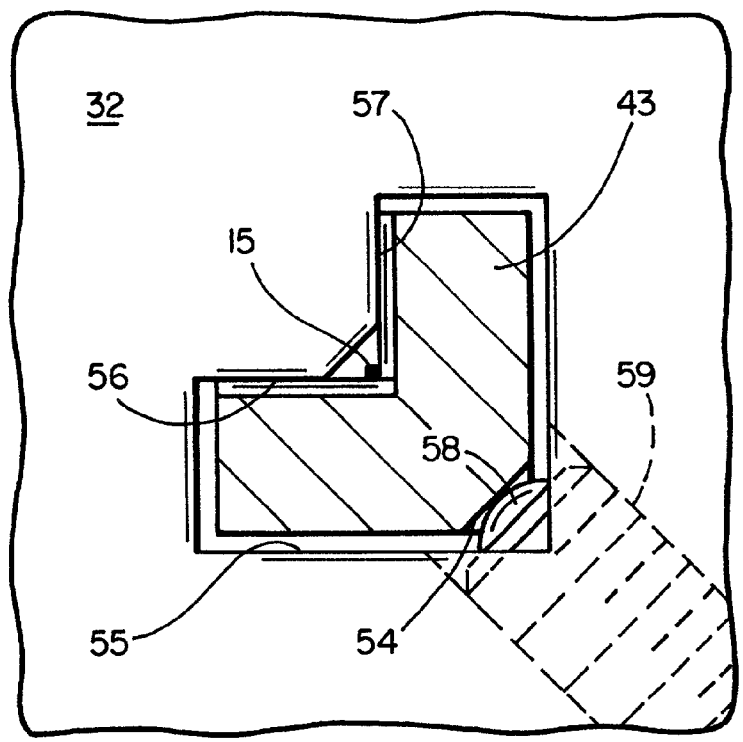
FIG_5
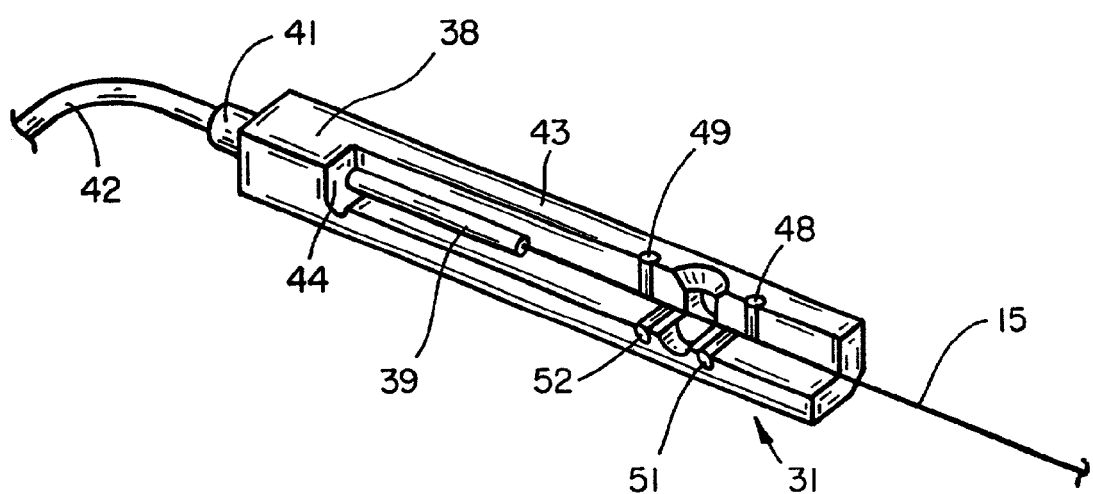
FIG_6

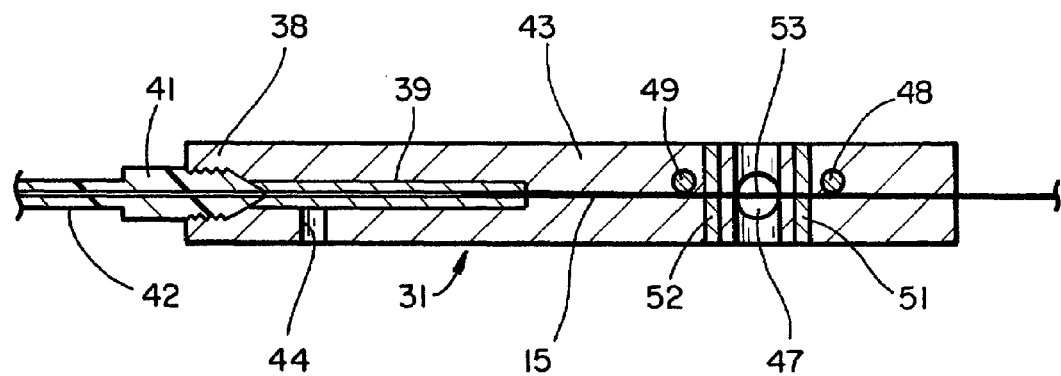
FIG_7
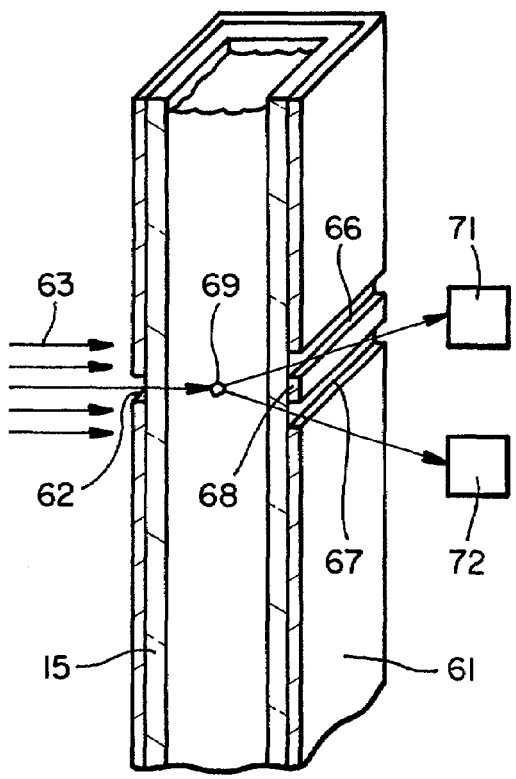
FIG_8
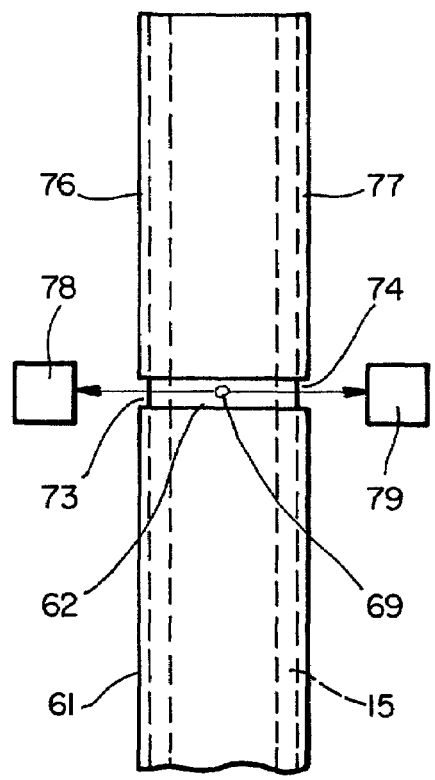
FIG_9

EXCHANGEABLE FLOW CELL ASSEMBLY WITH A SUSPENDED CAPILLARY

RELATED APPLICATIONS

This application claims priority to provisional application Ser. No. 60/291,541 filed May 16, 2001.

BRIEF DESCRIPTION OF THE INVENTION

This invention relates generally to flow cells for cytometers and particularly to flow cell assemblies with suspended capillaries and more particularly to flow cells which are easily replaceable or interchangeable.

BACKGROUND OF THE INVENTION

The detection and analysis of individual particles or cells in a suspension is important in medical and biological research. It is particularly important to be able to measure characteristics of particles such as concentration, number, viability identification and size. Individual particles or cells include, for example, bacteria, viruses, DNA fragments, cells, molecules and constituents of whole blood.

Typically, such characteristics of particles are measured using flow cytometers. In flow cytometers, particles which are either intrinsically fluorescent or are tagged and labeled with a fluorescent marker are caused to flow past a beam of radiant energy which excites the particles or labels or cells to cause emission of fluorescent light.

Conventional flow cytometry utilizes a flow cell that must be connected to a pressurized sample in order to force the sample into a flow cell cavity or lumen. The sample is then conducted by this pressure through the cavity or lumen, and then out the other end of the capillary into a sheath flow stream of buffer that is itself pressurized. This design requires complex flow cells that are expensive and require experts to install.

SUMMARY OF THE INVENTION

In the present invention, the sample is drawn through a suspended capillary. One or more photodetectors detect the fluorescent light emitted by the particles or labels responsive to an excitation beam of radiant energy at selected wavelengths as they move past the beam. The photodetectors respond to photons emitted by intrinsically fluorescent, tagged or labeled particles which flow through the beam to generate representative signals. A photodetector is also employed to measure light scattered by the particles to generate signals indicative of the passage and size of all particles which flow through the flow cell.

Such a cytometer is described in pending patent application Ser. No. 09/844,080 filed Apr. 26, 2001, which is incorporated herein by reference. The cytometer allows rapid analysis of single cells or particles by drawing the sample through a capillary tube for in-capillary optical detection. The sample is introduced to one end of the capillary by dipping the capillary into the sample while a source of vacuum is applied to the other end of the capillary. The sample is drawn through the capillary. This simple design lends itself to use of an easily exchangeable flow cell assembly which includes a capillary tube.

There is provided a flow cell assembly with suspended capillary which is replaceably mounted in the cytometer. The flow cell assembly facilitates the replacement of a flow cell with damaged or otherwise broken capillary with a cell with an undamaged capillary or with a flow cell having a different size or shape capillary.

The suspended capillary format of the cytometer allows sample aspiration by simply dipping the end of the capillary into the liquid sample. By providing a convenient means of replacing or exchanging flow cells, flow cells with damaged capillaries no longer require expert knowledge to repair. The use of simple twist-to-disconnect fluidic interconnects allows the flow cell to be easily freed from the rest of the fluidic system. By providing a simple locking device to constrain the flow cell, an untrained user can easily pull the flow cell free of the flow cytometer and replace it with another flow cell with an undamaged capillary with the capillary in the same optical position or to replace the flow cell with a capillary of different shape or size. By providing a precise positioning system, the replacement flow cell capillary can be located with such accuracy as to not affect the system's performance.

The flow cell/capillary replacement system allows users to quickly and affordably exchange a flow cell having a capillary of one size for a flow cell with a capillary of another size. This allows a user studying particles of one particular size to quickly reconfigure the cytometer for particles of a very different size. A flow cell with a capillary of one length may also be exchanged for a flow cell with a capillary of a different length. This allows the cytometer to be reconfigured for a wide variety of sample vial sizes. This also allows the introduction of flow cells having capillary passages long enough to reach samples contained in a well plate autoloader "docking station" below the cytometer. Users can exchange a flow cell having a capillary of one shape for a flow cell with a capillary of another shape. This allows, for example, a flow cell of a square cross-section to be replaced with flow cells of circular, rectangular, asymmetric or other cross-sections. Furthermore, this allows for forward compatibility with future innovations in the production of the flow cell tubing.

The simple flow cell/capillary replacement system allows cytometer users to quickly and affordably exchange a flow cell with certain properties for a flow cell with other properties. For example, future assays developed for use in flow cytometers may require capillaries with unusual properties such as resistance to certain corrosives or coatings to reflect, block or transmit light of various wavelengths. Also, future upgrades to the basic flow cell design such as masking to block light from reflecting and refracting off the capillary walls could be accomplished easily as such improvements become available.

BRIEF DESCRIPTION OF THE DRAWINGS

The invention will be more clearly understood from the following description when read in conjunction with the accompanying drawings in which:

FIG. 1 is a schematic diagram of a flow cytometer employing a flow-through capillary tube.

FIG. 2 is an elevational view of the flow cell assembly mounting block of the cytometer.

FIG. 3 is a perspective view of the exchangeable flow cell and mounting block.

FIG. 4 is a perspective view of the exchangeable flow cell and mounting block viewed at 180° from that of FIG. 2.

FIG. 5 is an enlarged sectional view of the mounting block with the flow cell mounted in the block taken generally along the line 5-5 of FIG. 4.

FIG. 6 is a perspective view of an exchangeable flow cell assembly.

FIG. 7 is a cross-sectional view of the exchangeable flow cell assembly of FIG. 6.

FIG. 8 is a perspective view of a rectangular capillary provided with masks for scatter detection.

FIG. 9 is a sectional view of a rectangular capillary with masks for fluorescence detection.

DESCRIPTION OF THE PREFERRED EMBODIMENT

Referring to FIG. 1, there is schematically illustrated a cytometer or particle analyzer 10 of the type disclosed in co-pending patent application Ser. No. 09/844,080 filed Apr. 26, 2001, incorporated herein by reference. As used herein, "particle" means particles or cells, for example, bacteria, viruses, DNA fragments, blood cells, molecules and constituents of whole blood. A fluid stream 11 with particles 12 flows in the direction indicated by the arrow 13. The sample or fluid stream is drawn through a capillary or tube 15 by a suitable pump. The capillary tube can take many shapes. It can be round, square, oblong, etc. A light source, such as laser 14, emits a light beam 16 of selected wavelength. The beam strikes particles which flow along the capillary. In order to count all particles which pass through the beam, light scattered by the particles is detected by an optical system including a detector 17, for example a photomultiplier tube. The detector provides an output signal such as that shown by the peak 18. The size and shape of the peak is dependent upon the size of the particle. The occurrence of the peak indicates that a particle has traversed the light beam.

If the particles are intrinsically fluorescent, or if the particles have been tagged or labeled with a fluorescent dye, they will emit light 21 at characteristic wavelengths as they pass through the beam 16. The light is detected at an angle with respect to the beam 16 so that no direct light is detected. The fluorescent light is directed to a beam splitter 22 which passes light above a given wavelength and reflects light below a given wavelength. Transmitted light is detected by detector 23 while reflected light is detected by the detector 24. For example, the beam splitter reflects light having wavelengths less than 620 nm and transmits light having a greater wavelength. Filters, not shown, may be placed in front of the detectors 23 and 24 to pass light at specific wavelengths, such as 580 nm and 675 nm, which will permit detection of particles tagged with readily available materials which emit light at predetermined wavelengths. The output of the detectors is shown as pulses 26 and 27. It should be appreciated that the foregoing description of a cytometer is not detailed and that an actual system will include optical elements to collect and direct the light. However, the foregoing explanation suffices in that it shows how the signals which are to be processed by the inventive signal processing system are obtained.

In the present invention, the capillary 15 is mounted in a flow cell assembly 31 which is received in a cytometer block 32 forming part of the cytometer instrument (not shown) which supports the light source 14, optics and photodetectors 17, 23 and 24. The block includes an opening 33 through which the excitation light beam 16 is projected. Scattered light 20 is detected by detector 17 by blocking direct light with a beam blocker 34. If the detector 17 is placed to detect side-scattered light, a beam blocker is not required. The fluorescent light 21 travels through a window 36. A shaft 35 is mounted on the block 32. The flow cell assembly 31 and cytometer block 32 are shown in more detail in FIGS. 3-7. The flow cell assembly 31 includes a body with a rectangular end 38 which accommodates a capillary tube union 39. The end 38 is threaded to receive a quick disconnect high pressure fitting 41 connected to the end of tubing 42. The other end of the tubing is connected to a syringe pump (not shown) which draws sample fluid through the capillary 15. When the flow cell assembly 31 is mounted in the block 32 the capillary 15 must be accurately located with respect to the light beam 16. To this end, the capillary must be accurately positioned in the flow cell body, and the flow cell and capillary must be accurately located in the cytometer block 32.

The flow cell body is machined to form an L-shaped region 43. This, together with the rectangular end 38, defines an overhang or stop 44 which engages a stop region 46 of the block 32, FIGS. 3 and 4. When the flow cell assembly is inserted into the block and the stops are engaged, portion 53 of the capillary is supported adjacent the light input aperture 47 in the body 43. Spaced reference pins 48, 49 and 51, 52 are mounted in the flow cell body and extend beyond the faces of the L-shaped cut-out. The capillary is positioned on the pins and secured to the shuttle such as by an adhesive. As a result, the portion 53 of the capillary is accurately located with respect to the flow cell body and aperture 47. Although the preferred embodiment includes locating pins, the body can be formed with spaced locating ridges. The outer edge of the body 43 has a camber 54 which helps guide the body as the flow cell is inserted in the block 32.

The block 32 includes an L-shaped opening 55 with reference surfaces 56 and 57. Spaced screws 59 with spring-loaded balls 58 extend through the wall of the block 32 into the L-shaped opening 55. The balls engage the flow cell camber 54 and urge it against the reference surfaces. To install a flow cell into the cytometer, the user places the end of the flow cell into the opening. As the flow cell body is moved down into the opening, the spring-loaded balls 58 urge the shuttle reference pins against the reference walls or surfaces 56 and 57. In view of the fact that the reference pins extend beyond the surface of the shuttle, they engage the reference surfaces and the capillary portion 53 is accurately located with respect to the light beam 16. The insertion is terminated when the stop 44 engages block stop 46.

A further improvement is to apply masks to the outer surface of the capillary. One mask includes a slit which passes a beam having a predetermined thickness. Referring to FIGS. 8 and 9, the mask 61 on the front face of the capillary includes a slit 62 which defines the thickness of the light beam from light source 63 traversing the capillary lumen. In the embodiment of FIG. 8, a mask is provided on the back face which includes spaced slits 66 and 67. The mask portion 68 between the slits 69 intercepts direct light. Light scattered by the particle 69 travels through the spaced slits and is detected by photodetectors 71 and 72. In the embodiment of FIG. 9, slits 73 and 74 are formed in masks 76 and 77 on opposite sides. Fluorescent emission from the particle 69 is detected by photodetectors 78 and 79. It is apparent that the masking arrangement of FIGS. 8 and 9 can be combined and both scattered light and fluorescent light can be detected with a single capillary.

Thus, there has been provided an improved exchangeable flow cell assembly which is easy to place in a cytometer with the capillary precisely located with respect to the light beam. The capillary may be masked to enhance the optics.

What is claimed is:

1. A flow cytometer comprising
    an exchangeable flow cell having a flow cell body and a capillary carried by and having one end extending beyond said flow cell body, wherein said flow cell body is provided with a recess extending along a portion of the length of the body, and includes means for accurately positioning the capillary in the recess along the length of the flow cell body, a block having an opening adapted to receive the exchangeable flow cell and being at least partially formed by two flat surfaces, wherein said positioning means engages said flat surfaces to position the capillary relative to the block, and said block includes means for urging the flow cell body against the flat surfaces, and a light source for emitting light to illuminate a portion of the capillary.

2. The flow cytometer of claim 1, wherein said flow cell body has an aperture in the recess for permitting light from said light source to illuminate a portion of the capillary.

3. The flow cytometer of claim 1, further comprising a pump for drawing a sample through the capillary.

4. The flow cytometer of claim 3 further comprising means for connecting said capillary to said pump.

5. The flow cytometer of claim 1, further comprising a pump for drawing a sample through the capillary.

6. The flow cytometer of claim 5 further comprising means for connecting said capillary to said pump.

7. The flow cytometer of claim 1 wherein the positioning means comprises spaced members which engage the capillary at spaced positions along the capillary.

8. The flow cytometer of claim 7 wherein said spaced members are provided on inside faces of said elongated recess and said capillary engages said members to be accurately positioned in said flow cell body.

9. The flow cytometer of claim 8 wherein said spaced members comprise crossed pins.

10. The flow cytometer of claim 1 wherein the capillary includes a mask having a slit through which light passes.

11. The flow cytometer of claim 10 wherein the mask is formed on the entrance wall of a rectangular capillary and a mask having spaced slits is formed on the opposite wall to pass light scattered by a particle or cell and block light traveling directly from the entrance slit.

12. The flow cytometer of claim 11 wherein the mask is formed on the entrance wall of a rectangular capillary and masks are formed on the side wall with slits which coincide with the entrance slit whereby fluorescent light emitted by a particle in the light beam travels through the slits for detection.

* * * * *